United States Patent
Ng et al.

(10) Patent No.: US 8,233,690 B2
(45) Date of Patent: Jul. 31, 2012

(54) DYNAMIC TOMOGRAPHIC IMAGE RECONSTRUCTION AND RENDERING ON-DEMAND

(75) Inventors: Susan Ng, Villanova, PA (US); Peter A. Ringer, Allentown, PA (US)

(73) Assignee: Real-Time Tomography, LLC, Villanova, PA (US)

( * ) Notice: Subject to any disclaimer, the term of this patent is extended or adjusted under 35 U.S.C. 154(b) by 780 days.

(21) Appl. No.: 12/323,889

(22) Filed: Nov. 26, 2008

(65) Prior Publication Data

US 2009/0274354 A1  Nov. 5, 2009

Related U.S. Application Data

(60) Provisional application No. 61/049,206, filed on Apr. 30, 2008.

(51) Int. Cl.
G06K 9/32 (2006.01)
G06K 9/34 (2006.01)
A61B 6/00 (2006.01)
A61B 5/05 (2006.01)
G06T 15/00 (2006.01)

(52) U.S. Cl. ........ 382/131; 382/154; 382/298; 382/254; 382/173; 382/260; 378/4; 378/21; 345/419; 600/425

(58) Field of Classification Search .................. 382/131, 382/128, 132, 154, 298, 254, 27, 283, 173, 382/260–264, 296, 228; 378/21, 4, 62; 345/419; 600/425

See application file for complete search history.

(56) References Cited

U.S. PATENT DOCUMENTS

| | | | |
|---|---|---|---|
| 4,969,110 A | 11/1990 | Little et al. | |
| 5,431,161 A | 7/1995 | Ryals et al. | |
| 5,640,436 A * | 6/1997 | Kawai et al. | 378/4 |
| 5,781,605 A | 7/1998 | Wohlrab | |
| 6,381,349 B1 | 4/2002 | Zeng et al. | |
| 6,845,144 B2 * | 1/2005 | Nishide et al. | 378/15 |
| 6,940,942 B2 | 9/2005 | Ullberg | |
| 7,564,937 B2 * | 7/2009 | Nakanishi | 378/4 |
| 2003/0099323 A1 | 5/2003 | Nagata et al. | |
| 2004/0066386 A1 | 4/2004 | Leprevost | |
| 2004/0070584 A1 | 4/2004 | Pyo et al. | |
| 2005/0226375 A1 | 10/2005 | Eberhard et al. | |
| 2006/0098856 A1 | 5/2006 | Botterweck et al. | |
| 2007/0036265 A1 | 2/2007 | Jing et al. | |
| 2007/0098141 A1 | 5/2007 | Hjarn et al. | |
| 2007/0110209 A1 | 5/2007 | Nishide et al. | |
| 2007/0165769 A1 | 7/2007 | Goto et al. | |
| 2007/0172104 A1 | 7/2007 | Nishide et al. | |
| 2007/0258558 A1 | 11/2007 | Nishide et al. | |
| 2008/0043024 A1 | 2/2008 | Schiwietz et al. | |
| 2009/0022387 A1 * | 1/2009 | Shirahata et al. | 382/131 |
| 2010/0239064 A1 * | 9/2010 | Zhou et al. | 378/9 |

* cited by examiner

Primary Examiner — Georgia Y Epps
Assistant Examiner — Magda Cruz
(74) Attorney, Agent, or Firm — Pepper Hamilton LLP

(57) ABSTRACT

A method of dynamically reconstructing three dimensional (3D) tomographic images from a set of projection images is disclosed. The method includes the steps of loading a set of projection images into a memory device, determining a reconstruction method for the set of projection images, reconstructing a 3D tomographic image from the set of projection images to be displayed to a user; and performing any post reconstruction processing on the 3D tomographic image.

33 Claims, 13 Drawing Sheets

DYNAMIC TOMOGRAPHIC IMAGE RECONSTRUCTION AND RENDERING ON-DEMAND

RELATED APPLICATIONS AND CLAIM OF PRIORITY

This application claims the priority benefit of U.S. Provisional Application No. 61/049,206 filed Apr. 30, 2008 which is hereby incorporated by reference.

NOT APPLICABLE

BACKGROUND

The present invention is related to the field of image reconstruction in digital x-ray tomography or tomosynthesis, and more particularly, to the reconstruction of three-dimensional (3D) tomographic images in digital tomography or tomosynthesis using a graphics processing unit (GPU).

Tomography is imaging by sections or sectioning an object into multiple images, and reconstructing the images to view an object of interest. The advantage of tomography over conventional x-ray imaging is that it eliminates the superimposition of images of structures and tissues outside the area of interest.

Today, projection mammography is considered the gold standard for the detection of breast cancer. However, both film-screen and digital mammography are subject to a number of fundamental limitations related to the projection process, whereby two-dimensional (2D) images are produced of the 3D breast anatomy. As a result, mammography superimposes normal tissues resulting in artifactual densities that often necessitate a biopsy; this leads to a loss in specificity. In addition, true lesions may be masked by the superimposed normal tissue and thereby rendered undetectable; this reduces the sensitivity of mammography.

Tomographic x-ray breast imaging would obviate these limitations. Preliminary studies of breast tomosynthesis have demonstrated a 16% increase in sensitivity and 85% decrease in false positives as compared to digital mammography. It is widely believed that digital breast tomosynthesis (DBT) has the potential to replace mammography (both digital and film) in the future, based on preliminary clinical results.

In Digital Tomosynthesis, a 3D tomographic image of an object is reconstructed from a limited set of 2D radiographic projection images. A digital tomosynthesis system includes one or more x-ray sources and one or more one-dimensional (1D) or 2D x-ray digital detectors. In the most common form of digital tomosynthesis, an x-ray source is rotated by a gantry in an arc through a limited range of angles about a pivot point. A set of projection radiographs of the object are acquired by the detector at discrete locations about the x-ray source. In other embodiments, the source may be held stationary while the detectors are moved, or the source and the detector may both move.

FIGS. 1A-1D illustrate various examples of image acquisition geometries. FIG. 1A shows the most common acquisition geometry. In this acquisition system, the x-ray focus ($F_i$) is positioned sequentially at multiple locations ($F_1, F_2, F_3, \ldots$). At each location ($F_i$), a projection image of the acquired anatomy (in this case, the breast) is made onto the detector to produce an image ($D_i$). A lesion (shown as a dot in plane R) will be projected to different locations on the detector. When backprojected, the various images will add coherently in the tomosynthesis image of plane R to reconstruct the lesion. For illustration, the x-ray foci ($F_i$) are shown in an arc with equal spacing; in fact, the location and spacing of the x-ray foci may be arbitrary. Similarly, the detector is shown to be held rigidly; again, this is only for the purposes of illustration; the detector may also be oriented in an arbitrary manner.

FIG. 1B shows a second acquisition geometry. In this example, detector (D) rotates as the x-ray focus ($F_i$) moves through a limited range of angles. A lesion (again shown as a dot in plane R) will be projected to different locations on the detector. When backprojected, the various images will add coherently in the tomosynthesis image of the plane R to reconstruct the lesion. In FIG. 1B, the x-ray detector is shown perpendicular to the central axis of the x-ray beam. However, the angle of the x-ray detector to the central axis of the x-ray beam can be arbitrary. Also, the spacing and location of the x-ray foci F can be arbitrary. This geometry is similar to that described in Patent Application Publication No. US 2007/0036265.

FIG. 1C shows a third example acquisition geometry. In this example, both the x-ray source (F) and a set of linear detectors ($D_i$) move continuously along an axis. The system includes a pre-collimator (P) to define the x-ray beam as it passes through the patient. Each line detector records a linear image of radiation as transmitted through the anatomy at a unique angle and position. A plurality of 2D images may be formed, where each 2D image is formed from a plurality of line images as recorded by a single one of the line detectors. Note that only 5 linear detectors are shown in FIG. 1C for clarity. This geometry is similar to that described in U.S. Pat. No. 6,940,942.

FIG. 1D shows a fourth example acquisition geometry. In this example, the x-ray focus is moved continuously while a small number of discrete linear detectors produce a sequential set of linear images of the anatomy. Note that only a small number of acquisition locations are shown for clarity. This geometry is similar to that described in Patent Application Publication No. US 2007/0098141.

Regardless of acquisition geometry used, after the projection images are acquired, they are reconstructed into a set of 3D tomographic images that are saved and then reviewed at a later time.

FIG. 2A illustrates the prior art technique for viewing images. In step 202, all 3D tomographic images are reconstructed at fixed increments (e.g., 1 mm for tomosynthesis to 3 mm for CT). Once a 3D image dataset is reconstructed, the images are saved at step 204. Once saved, the process proceeds to step 206 whereby a user (e.g., a radiologist) views the images at a later time. If the user wishes to change any of the reconstruction parameters used to process the images, the process may begin again and a new set of 3D tomographic images must be reconstructed. This reconstruction method is essentially an off-line approach.

After the projection images are acquired, they must be reconstructed into 3D tomographic images. Iterative tomosynthesis reconstruction methods, such as algebraic reconstruction techniques and maximum likelihood estimation maximization, generally involve reconstructing a 3D) tomographic image of the full imaged volume. These techniques provide good image quality but are computationally expensive as they generally involve an initial reconstruction followed by iterative updates of the full 3D image dataset until a threshold criterion is met. In DBT, typical reconstruction times vary from 5 to 30 minutes to reconstruct one 3D image dataset per breast.

Single-pass reconstruction techniques used in tomosynthesis do not generally require a reconstruction of the full 3D image dataset and may thus be computationally efficient. Single-pass reconstruction allows reconstruction of a 3D tomographic image in a single iteration consisting of a set of reconstruction steps. In this example, a set of reconstruction steps is defined as the performance of steps 202 and 204 as these steps may be iteratively performed numerous times, each time resulting in the reconstruction of a single image. Examples of single-pass reconstruction techniques are shift-and-add algorithms and simple backprojection in which 2D projection images are spatially translated with respect to each other through the image plane (hence the name "backprojection") to obtain a rough approximation of the original. The projections interact constructively in regions that correspond to the structures in the original object. Structures not in the reconstructed image plane are blurred. Filtered backprojection (FBP) is another backprojection method in which the projection images are filtered prior to reconstruction.

Each of these conventional reconstruction techniques has inherent drawbacks, e.g., poor image quality, lengthy computational time, extensive required filtering. By maintaining a large number of image files for reconstruction, each technique is also highly demanding on a central processing unit (CPU), thereby causing additional processing delays. Several approaches have been attempted to overcome these drawbacks, such as application specific integrated circuits (ASICs) of specifically designed field programmable gate arrays (FPGAs), which is a device that can be configured to perform a specific task. Both these approaches are expensive though, as the ASICs or FPGAs are designed for a single, specific purpose and do not provide much, if any, additional scalability.

Graphic Processor Units (GPUs) are pipeline processors, designed to accelerate the graphics rendering pipeline. Many of the gains in GPU performance have arisen from the ability to parallelize the various elements of the pipeline. Traditionally, the GPU architecture included vertex processors, called vertex shaders, which were specialized for geometric computations, and pixel processors or pixel shaders which were specialized for point operations. More recently, GPUs have been based upon a unified shader architecture in which unified processors will switch between the two types of shaders depending on the work that needs to be done.

Graphics objects are typically composed of polygon meshes, where additional surface detail can be modeled by mapping images or textures onto the polygons during the rendering phase. Texture mapping is a technique for efficiently modeling a surface's properties and is an efficient way to provide intricate surface detail without increasing an object's polygon count. GPUs are highly optimized to perform texture mapping very quickly, even under perspective distortion.

Modern GPUs are organized in a manner similar to that of GPU 300 shown in FIG. 3. The input to the pipeline is a list of geometric objects specified by vertices and temporarily stored in a vertex buffer 302. A vertex is the point intersection of two sides of a polygon. The vertices are transformed to the object's position in 3D space and projected to the screen plane by vertex shaders 304. The projected vertices are then assembled into triangles in the screen space and sent to the rasterizer 306. Rasterizer 306 produces zero or more fragments, one fragment for each pixel covered by the triangle. One or more pixel shaders, or in this example fragment processor 308, calculates the color (or shade of gray) for each fragment, typically using values from the texture memory 312. Finally, for each fragment, a pixel is written to the frame buffer 310 or back to texture memory 312.

With recent advances in GPU performance and architecture, GPUs are now increasingly being used as cost-effective high-performance co-processors for scientific computing and medical imaging. Primarily designed to deliver ultra-high definition graphics for video games in real-time. GPU performance has been increasing at a rate triple to Moore's Law in the last 10 years and is currently over an order of magnitude faster than that of CPUs. In addition, new generation GPUs offer programmability at floating point precision. For these reasons. GPUs are increasingly being used as cost-effective high-performance co-processors for scientific computing and medical imaging.

STATEMENT REGARDING FEDERALLY SPONSORED RESEARCH OR DEVELOPMENT

This invention was made with U.S. Government support under SBIR Grant EB007140 awarded by the National Institutes of Health. The U.S. Government has certain rights in the invention.

SUMMARY

This document describes a technique for dynamically reconstructing and viewing three-dimensional (3D) tomographic images, a method for directly reconstructing 3D tomographic images from projection images acquired in tomosynthesis or tomography. The method allows for preprocessing of the projection images and reconstruction of the projection images using a backprojecting and filtering (BPF) method in which the projection images are backprojected into a 3D tomographic image and then filtered to enhance specific structures in the resultant 3D tomographic image.

In one general respect, the embodiments disclose a method of dynamically reconstructing 3D tomographic images from a set of projection images. The method includes the steps of loading a set of projection images into a memory device, determining a reconstruction method for the set of projection images, applying any necessary preprocessing, reconstructing a 3D tomographic image from the set of projection images to be displayed to a user; and performing any post reconstruction processing on the 3D tomographic image.

In another general respect, the embodiments disclose a second method of dynamically reconstructing 3D tomographic images from a set of projection images. The second method includes the steps of loading a set of projection images into a memory device, determining a reconstruction method for the set of projection images, determining a region of interest in the set of projection images, applying any necessary preprocessing, reconstructing a 3D tomographic image from the set of projection images focusing on the determined region of interest to be displayed to a user, and performing any post reconstruction processing on the 3D tomographic image.

In another general respect the embodiments disclose a third method of dynamically reconstructing 3D tomographic images from a set of projection images. The third method includes the steps of loading said set of projection images into memory, selecting a region of interest, applying any necessary preprocessing, selecting a reconstruction method reconstructing an image according to said reconstruction method to produce a 3D tomographic image focusing on said region of interest, performing any post reconstruction processing on the 3D tomographic image, and rendering said 3D tomographic image on a display.

DETAILED DESCRIPTION

Before the present invention is described, it is to be understood that this invention is not limited to the particular systems, methodologies or protocols described, as these may vary. It is also to be understood that the terminology used herein is for the purpose of describing particular embodiments only, and is not intended to limit the scope of the present disclosure which will be limited only by the appended claims.

It must be noted that as used herein and in the appended claims, the singular forms "a," "an," and "the" include plural reference unless the context clearly dictates otherwise. Thus, for example, reference to an "image" is a reference to one or more images and equivalents thereof known to those skilled in the art, and so forth. Unless defined otherwise, all technical and scientific terms used herein have the same meanings as commonly understood by one of ordinary skill in the art. As used herein, the term "comprising" means "including, but not limited to."

It should also be noted the principles and embodiments discusses herein are not limited by the examples provided. References to breast and digital breast tomosynthesis (DBT) are given merely by way of example, and the processes, principles and embodiments disclosed herein can be applied to any body part or inanimate object.

The present invention is (1) an optimized dynamic reconstruction and rendering algorithm for tomographic image reconstruction on-demand, (2) an optimized and dynamic image reconstruction method incorporating a backprojection and filtering (BPF) algorithm in which a reconstructed image is filtered after backprojection, and (3) an optimized method for tomographic image reconstruction using a graphics processing unit (GPU).

The following discussions focus on a dynamic reconstruction and rendering (DRR) algorithm for tomosynthesis and tomographic imaging. In DRR, a 3D tomosynthesis or tomographic image is reconstructed in real-time and on-demand using the region of interest (ROI), the parameters for reconstructing the image and the display settings selected by the user within an interactive graphical user interface (GUI).

The DRR approach is applicable to any imaging task in which off-line reconstruction is currently required provided that an equivalent rapid method of reconstruction exists. Other examples of suitable imaging methods include static computed tomography (CT) imaging methods such as axial CT, helical CT and cone-beam CT, as well as dynamic CT imaging methods such as CT fluoroscopy, CT perfusion, other four-dimensional (4D) CT techniques and MRI imaging using appropriate image acquisition pulse-sequences.

Figure 2B:
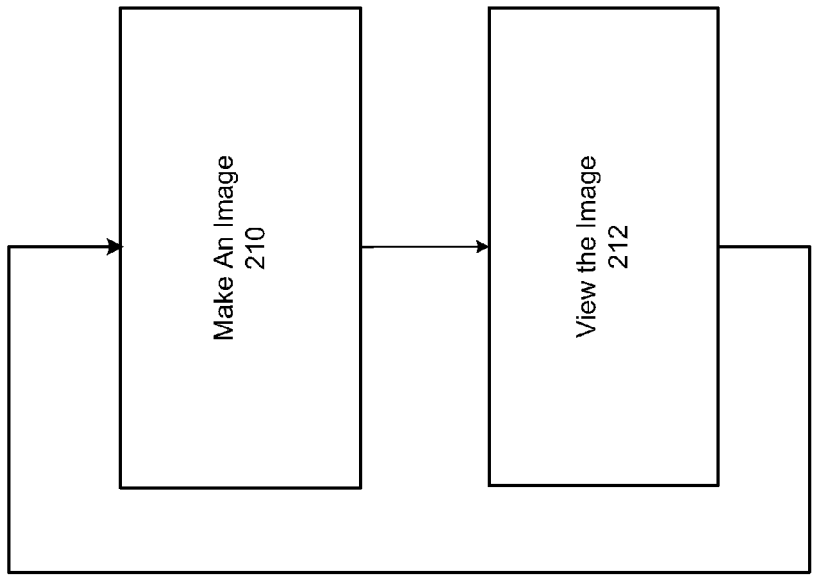
FIGS. 2a and 2b illustrate an example of image reconstruction and viewing according to principles of the present invention as compared to prior art techniques.
Figure 2A:
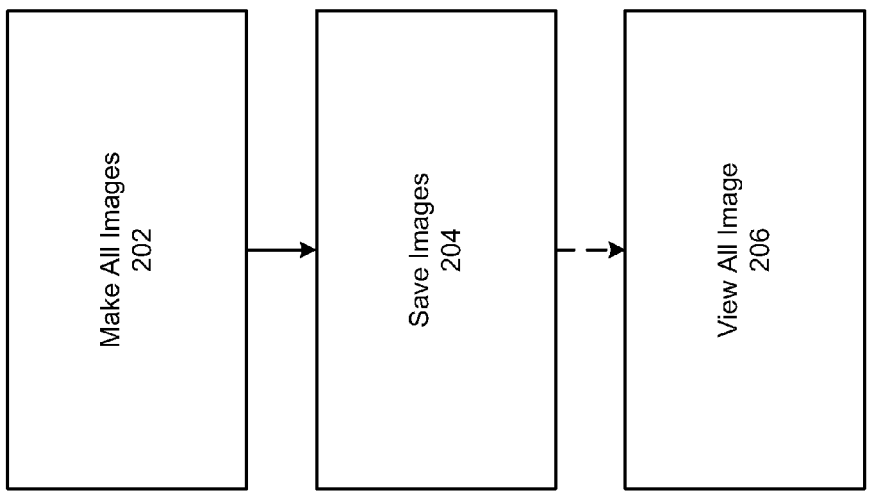
Figure 3:
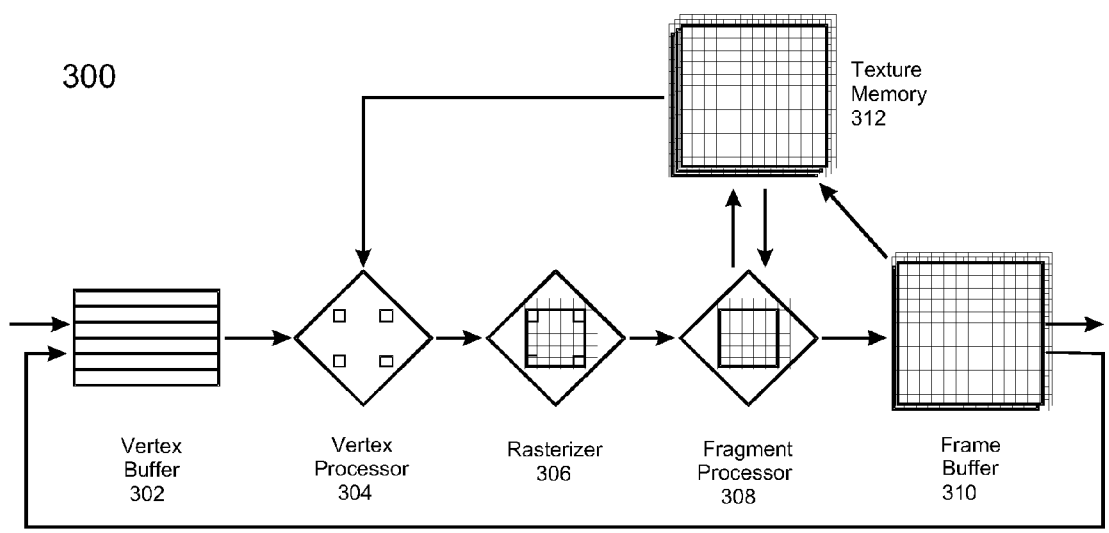
FIG. 3 illustrates an exemplary graphics processing unit.

FIGS. 2a and 2b illustrate the differences in imaging approaches between prior art (FIG. 2a, discussed above) and DRR (FIG. 2b). Prior art methods are essentially off-line approaches in which images are processed, saved and then reviewed at a later time. With DRR, the reconstruction of a 3D tomographic image is completely responsive to the reviewer. Although relatively simple, it is a fundamentally different approach compared to prior art tomographic imaging methods. DRR requires a different mindset with respect to tomographic images.

FIG. 2b illustrates an exemplary embodiment of the DRR approach. The process begins at step 210 where a single 3D tomographic image is reconstructed in response to a change in a reconstruction parameter(s). Once the 3D tomographic image is reconstructed, it is immediately available for viewing by a user at step 212. If the user changes the ROI or any other parameter the process returns to step 210 where only the image is reconstructed for the specified ROI, resulting in a dynamically produced 3D tomographic image in response to a user's commands.

In addition to dynamically producing tomographic images, there are many advantages to DRR, including better image quality, improved diagnostic accuracy, more efficient clinical workflow, reduced data storage and real-time applications, such as image-guided procedures.

Figure 4:
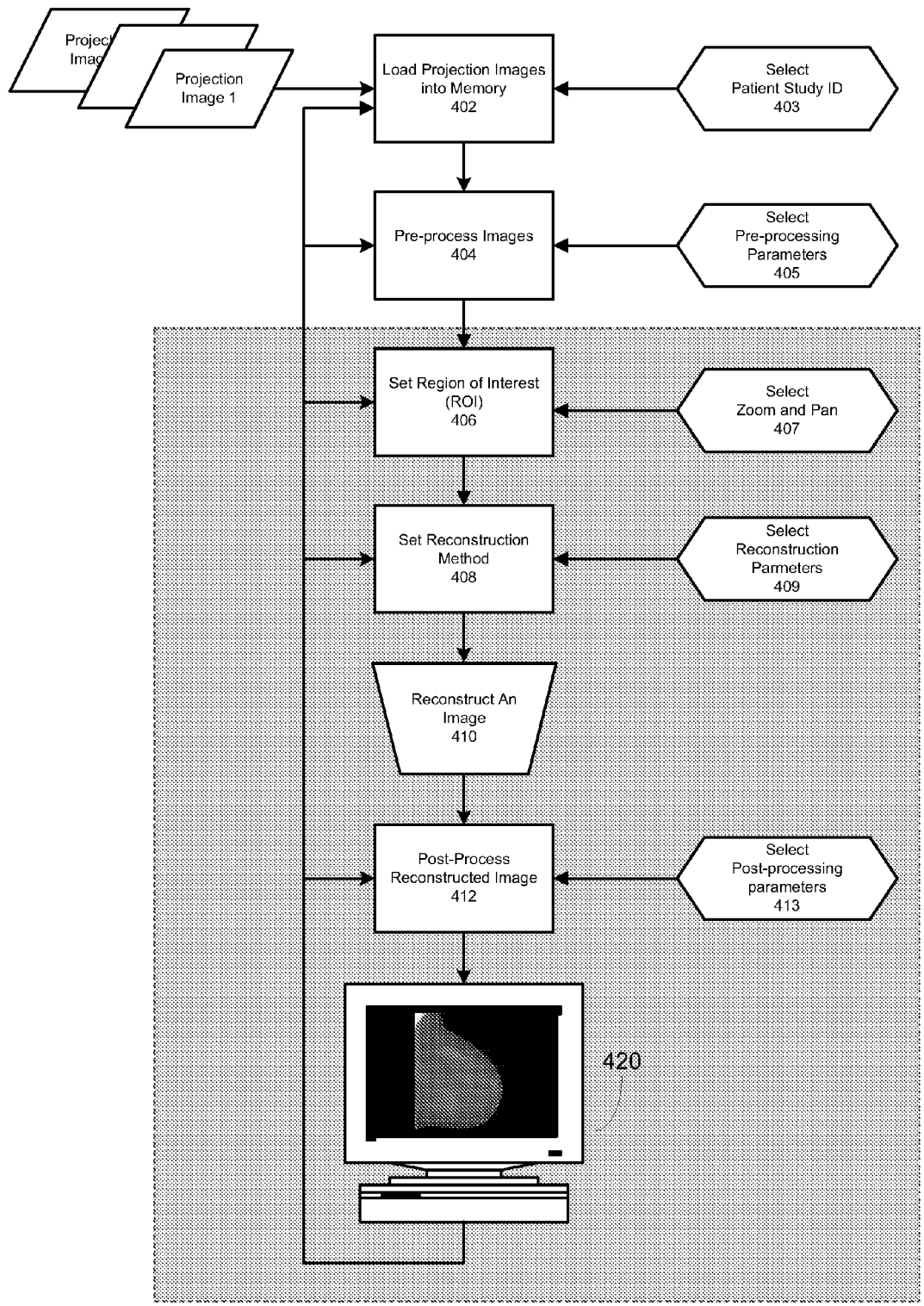
FIG. 4 illustrates an exemplary schematic of a dynamic reconstruction and rendering technique according to an embodiment of the present invention.

FIG. 4 illustrates an exemplary schematic of the DRR approach. In this approach, the image reconstruction and rendering are intimately interlinked. Requested alterations to the image (e.g., field of view, plane of reconstruction, filter, etc.) result in a new image being dynamically reconstructed and rendered. This approach is possible today because of significant advances in computational efficiency. It does, however, require a new mindset "reconstruction on-demand"—and careful algorithm design and implementation optimization in order to achieve real-time performance. This necessitates a reconstruction algorithm that can reconstruct images at video refresh rates (discussed in more detail below).

The DRR process begins at step 402. Here, each projection image is loaded into memory. Alternatively, each image may be in memory after acquisition. Once the images are in memory, the process moves to step 404. Here, any preprocessing is performed on the images. Preprocessing steps may include rescaling the image data to be proportion to the logarithm of the x-ray fluence, normalizing the image data segmenting the image data, masking defects in the image data, apodization of the image data and thickness equalization. Preprocessing is distinguished from other subsequent processing in that it typically does not need to be altered in subsequent steps of the algorithm. The images are preprocessed again only if the preprocessing parameters are changed or a new study is loaded.

Next the process proceeds to step 406. Here, a single 3D tomographic image is reconstructed for a specific region of interest. The ROI is typically defined as a plane segment in 3D, thus both the position of the plane and the extent or "field-of-view" of the display region need to be specified.

In prior art, the planes of reconstruction are fixed, while in DRR the plane of reconstruction is arbitrary. The DRR method enables the user to specify the exact plane of the image to be reconstructed. This ability is one of the primary advantages for DRR. Prior art tomographic reconstruction and display methods reconstruct images in fixed increments (typically, 3 mm for computed tomography and 1 mm for breast tomosynthesis). The result is that an object that is centered between the two reconstructed slices is blurred. With DRR, the image may always be reconstructed so that the object is exactly in focus because the selection of the reconstructed slice plane is arbitrary and set by the user at the time of display. Thus, the blurring from the fixed slice spacing is eliminated. DRR will result in sharper images.

In prior art, the field of view is preset depending upon the clinical application (e.g., by the body part size). The number of pixels in the image is typically determined as a tradeoff between the stored image file size, the type and nature of the image acquisition, and the noise in the acquired data. Typical CT data sets have an in-plane matrix size of 512×512 pixels. Magnetic resonance data sets may have in-plane matrix sizes from 128×128 to 512×512 pixels.

In DRR, the ROI is dynamically selectable by the user, for example by specifying the image pan, zoom and depth settings. Zoom is the ability to change the magnification level of the image that the user wants to view the image. This view may appear to be close up (zoomed in) or far away (zoomed out). Pan is the ability to change the area of the image to be viewed.

In prior art, zooming may be achieved in two different ways. First, it is possible to reconstruct the image to a new field-of-view. As with other alterations to conventional reconstructions, this action requires that the raw data be available and that the images be reprocessed again off-line. As a result, a delay in the diagnosis will occur while the physician waits for the reconstruction to complete and the resultant data are transmitted to the review workstation. Alternatively, an electronic zoom may be applied to the currently available image data. However, in this instance, there is no improvement of image quality; rather, the image is simply displayed larger on the screen.

With DRR, the ROI is directly incorporated into the image reconstruction to avoid unnecessary computation. This is an important advantage over the prior art reconstruction techniques. The ROI for reconstruction and display is defined by the image area specified in the pan setting, the magnification level specified in the zoom setting and the position of the plane of reconstruction specified in the depth setting. The ROI is mapped to the screen; no calculations are performed outside the ROI. The level of detail in the image is determined by the size of the region of the computer screen used to display the image (in pixels), and the size of the ROI (as measured physically in the anatomy in units of length).

Note that prior art techniques for displaying images with zooming and panning do not result in improved image quality, rather the image is simply made larger or smaller; thus, the data encoded in the originally reconstructed images is unaltered. However, DRR results in a fundamental difference. Altering the ROI (by changing the pan, zoom or depth) results in the image being newly reconstructed. The result is a "true magnification" in which real, obtained data is displayed, not merely interpreted data as is common in the prior art; thus, the data displayed is new and potentially diagnostically informative.

Once the ROI is selected, the process proceeds to step 408. Here, reconstruction parameters may be selected by a user in step 409. Once the reconstruction parameters and ROI are selected, the process proceeds to step 410 where the 3D tomographic image is reconstructed.

After the image is reconstructed, the process proceeds to step 412 where post-processing is applied to the 3D tomographic image. Post-processing can including image filtering, pixel inversion, flipping, rotation, statistical conditioning such as de-noising, as well as changing the window width and window level, thereby adjusting the gray levels of an image. These post-processing parameters may be selected by a user.

One advantage of DRR is it enables the radiologist to dynamically change the reconstruction filter when reviewing the 3D image. Different filters enhance different clinical indications of tissue and facilitate the diagnosis and 3D localization of radiographic findings. This has the potential to increase an observer's clinical performance. As mentioned in previous sections, the benefit of post-processing filtering is that only the reconstructed image needs to be filtered instead of all projection images. Filtering during post-processing can result in better image quality because all image data is preserved in the reconstructed image. Additionally, different filters may be applied dynamically as the ROI is dynamically changed in DRR.

Following the post-processing in step 412, the image is rendered and displayed at step 420. In a typical embodiment, DRR is implemented on a computer with an interactive GUI much like other medical viewing software the GUI contains the window(s) in which image(s) are displayed and the interface that permits the user to enter commands and information into the computer through input devices such as a keyboard or a pointing device.

FIG. 4 further illustrates a sample schematic of potential features that may be presented to a user of an interactive GUI. Here, the user is presented with options to select a case by indicating a patient study ID 403, specify preprocessing parameters 405, select zoom and pan parameters 407, specify reconstruction parameters 409, and specify filters and any post-processing 413. DRR processes these commands and produces the results dynamically. A preset combination of reconstruction parameters and filters can be defined for ease of use and convenience.

The user may be presented with additional options beyond, or not directly related to, the image reconstruction or quality. For example, a user may be presented with the option to toggle between projection and reconstruction images. This operation allows clinicians to view the reconstructed image and each projection image at the same geometry, location and region of interest. This facilitates the localization of structures of interest in both the projection images and the reconstructed image and could potentially assist radiologists in understanding the morphology of these structures and, hence, diagnosis. Additionally, technologists may check image quality by verifying the contributions of each projection image to the reconstruction image.

Additionally, a user may be allowed to save a selected set of images to record pertinent clinical findings or a complete set of images is allow DRR generated images to be viewed on a non-DRR equipped review workstation. The typical embodiment of DRR would allow the clinician to save clinically relevant images when viewing each case and to export tomographic images from the review workstation to a foreign workstation.

In both instances, the DRR software may be used to reconstruct and save or to forward images reconstructed in a manner similar to that used in prior art (i.e. reconstructed in fixed increments with one or more filters applied). Given the expected speed of reconstruction, reconstructions could be performed in real-time as the data is being exported, so that it should not be necessary to store reconstructed images by default (the selected images could be stored by recording the reconstruction geometry and filters only).

One of the distinguishing features of DRR is the immediate responsiveness of the image reconstruction to altered parameters. This feature necessitates a fast reconstruction algorithm that will reconstruct a tomographic image at video refresh rates (approximately ¹/20-¹/60 sec.). The use of any of the reconstruction algorithms in DRR requires careful algorithm design and implementation optimization such that real-time performance is achieved.

In traditional tomosynthesis or tomography, several methods are used to reconstruct 3D images. The most common method for reconstructing 3D tomographic and tomosynthesis images is Filtered Backprojection. Other types of reconstruction methods include multi-pass or iterative reconstruction as well as Fourier reconstruction. However, each of these reconstruction methods has drawbacks including poor image quality, lengthy computational time, and extensive required filtering.

Single pass reconstruction algorithms, such as FBP, are generally preferred as they are less computationally expensive and therefore faster. Iterative and Fourier techniques are applicable when optimized and implemented on dedicated fast hardware, such as GPUs, application specific integrated circuits (ASICs) or field-programmable gate arrays (FPGAs). With iterative and Fourier techniques, filtering is applied to the projection images before reconstruction.

Figure 5:
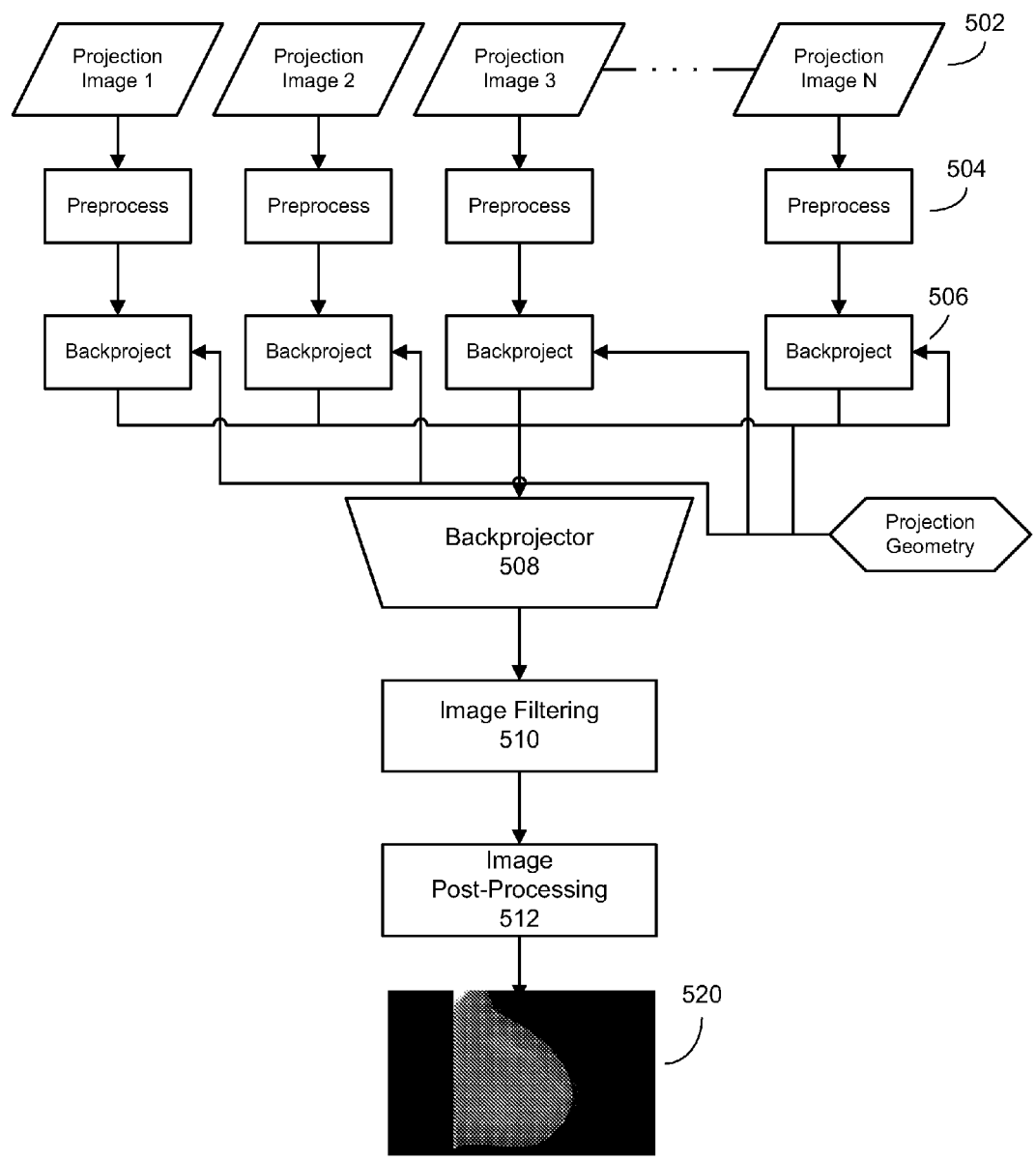
FIG. 5 illustrates an example of a backprojection and filtering algorithm according to one embodiment of the present invention.

An exemplary reconstruction method that enables on-demand DRR is the Backprojection and Filtering (BPF) method, as illustrated in FIG. 5 (discussed in detail below). It should be noted though this is for exemplary purposes only, and any fast reconstruction method that enables the fundamental DRR key features may be used.

The BPF method is well-suited to DRR compared to the other backprojection methods, such as FBP, because only the reconstructed image is filtered whereas all the projection images must be filtered in FBP prior to back projection. Thus, BPF is potentially faster depending on the level of filtering of the image sets. The advantage of BPF is that for each image reconstructed, only one image is filtered instead of having to filter all the source projection images prior to backprojection, as is required in FBP. This results in a faster reconstruction time for BPF and real-time reconstruction. The disadvantage of FBP is that if the radiologist needs to view the images reconstructed with different filters or other parameter changes to observe different clinical indications, all the images have to be reconstructed again.

A second advantage of BFP is, by filtering after reconstruction, the reconstructed image contains all the imaging information from the projection images so that statistical conditioning and non-linear filters may be applied to the reconstructed image. For example, if the data are filtered before backprojection, the gray scale values no longer reflect the x-ray intensity, thus resulting in loss of image quality in the reconstruction.

In FBP, the filtering operation will introduce artifacts into the data (due to large changes in x-ray attenuation) that will be propagated throughout the reconstructed image during backprojection. As the filtering in BFP is performed after backprojection, no artifacts are introduced into the source projection data.

A third advantage is that BPF enables dynamic real-time reconstruction and rendering of tomographic images (discussed in detail above). In DRR, one tomographic image is reconstructed on-demand and any reconstruction parameters (e.g. filters, ROI, and display parameters) may be changed in real-time.

FIG. 5 is an exemplary flow diagram of one exemplary BPF algorithm. The algorithm begins at step 502, where, prior to preprocessing, each projection image is loaded from disk into memory, if not already in memory. Next, at step 504, each of the loaded images is preprocessed. There may be several reasons to preprocess the data. One reason may be to optimize the time it takes to reconstruct the images by rejecting data that is invalid and process only data that will contribute to a fully reconstructed image.

In the present invention, preprocessing may include one or all of the following preprocessing steps. Additionally, as the art of digital tomosynthesis and image processing advances, additional preprocessing steps may be added. The following preprocessing steps are therefore shown only by way of example. Similarly, although a preferred ordering of these preprocessing steps is given, these steps may be conducted in any order.

It should be noted in the following discussion it is presumed that the x-ray detector has been calibrated at each acquisition angle. Such calibration typically consists of dark field, bright field, dead-pixel correction and non-linearity corrections.

During the preprocessing step 504, one or more of the following steps may be performed: resealing the image data to be proportion to the logarithm of the x-ray fluence; normalizing the data; masking defects in the image data; apodizing the data; segmenting the data; and applying thickness equalization.

When normalizing the data a fast approximation for equalizing the x-ray intensity of each source projection image to account for the increased attenuation at oblique angles is to assume parallel x-rays. Under this assumption, a single angle is used to normalize the projection data from a single source position. A more accurate method accounts for the divergent nature of projection radiography. In this method, the angle of incidence of each x-ray beam is calculated and is used to normalize the projection data.

Image data defects are dependent on the type of acquisition system. For example, the image data defects due to x-ray collimation when the x-ray source is at large angles with respect to the detector normal may be masked so as to not be included in the reconstruction. In these cases, the primary x-rays from an x-ray source would not interact with the detector and, as a result, no valid information is recorded in the detector at those locations. The likelihood of invalid data occurring is greater at the extreme angles.

There may be numerous potential reasons for segmenting the data. One reason may be to identify tissues in the projection images that require specific processing. Another reason may be to identify areas of invalid data or the air surrounding the anatomy to reduce processing time.

Apodizing the data may be used to smooth the transition from regions of valid data to regions of invalid data. This will avoid artifacts from occurring in the reconstructed 3D tomographic images at the edges of the valid data areas.

Weightings may be used to mask defect areas and to apodize the data. Weightings are assigned to each pixel in the source projection image. Where defects exist, the weighting is set to a known value. Near the edges of areas of defective data, the weightings are adjusted to apodize the data.

In DBT, the source projection images may be preprocessed to segment the breast from the air. Once the boundary of the breast is determined, the region outside the breast may be masked or a peripheral equalization may be applied to the breast data.

In DBT, peripheral equalization compensates for the reduction in thickness at the outer edge of the breast in the image. In 2D mammography and DBT images, the peripheral area of the breast tends to have higher intensity than the central area of the breast. This is due at least in part to the fact that the thickness of the compressed breast decreases from the central area to the peripheral area. Peripheral equalization balances the intensity of the peripheral and central areas of a breast image.

After preprocessing, the algorithm proceeds to step 506 where the image is backprojected. In this step, the projection images are backprojected using the geometry of the acquisition system and then combined to produce a tomographic image. Combinations of backprojection logic or "backprojectors" have been implemented, which may be used separately or combined, are described below.

There are many embodiments of the backprojector which may contain both mathematical and logic operations. Different backprojectors are developed for a variety of purposes including reducing image artifacts, enhancing elements in the image, decreasing reconstruction time, etc.

One sample backprojector is a "simple backprojector". For each projection image, a projective geometry is constructed to mimic the x-ray acquisition geometry for that image. The detector plane is backprojected to the plane of reconstruction according to the specified geometry. The projection image is then mapped to the reconstructed plane. This is implemented by parameterizing the geometry in terms of a 3×4 projective matrix, A, such that $$\begin{pmatrix} u \\ v \\ s \end{pmatrix} = \begin{pmatrix} a_{11} & a_{12} & a_{13} & a_{14} \\ a_{21} & a_{22} & a_{23} & a_{24} \\ a_{31} & a_{32} & a_{33} & a_{34} \end{pmatrix} \begin{pmatrix} x \\ y \\ z \\ t \end{pmatrix}$$

Figure 1A:
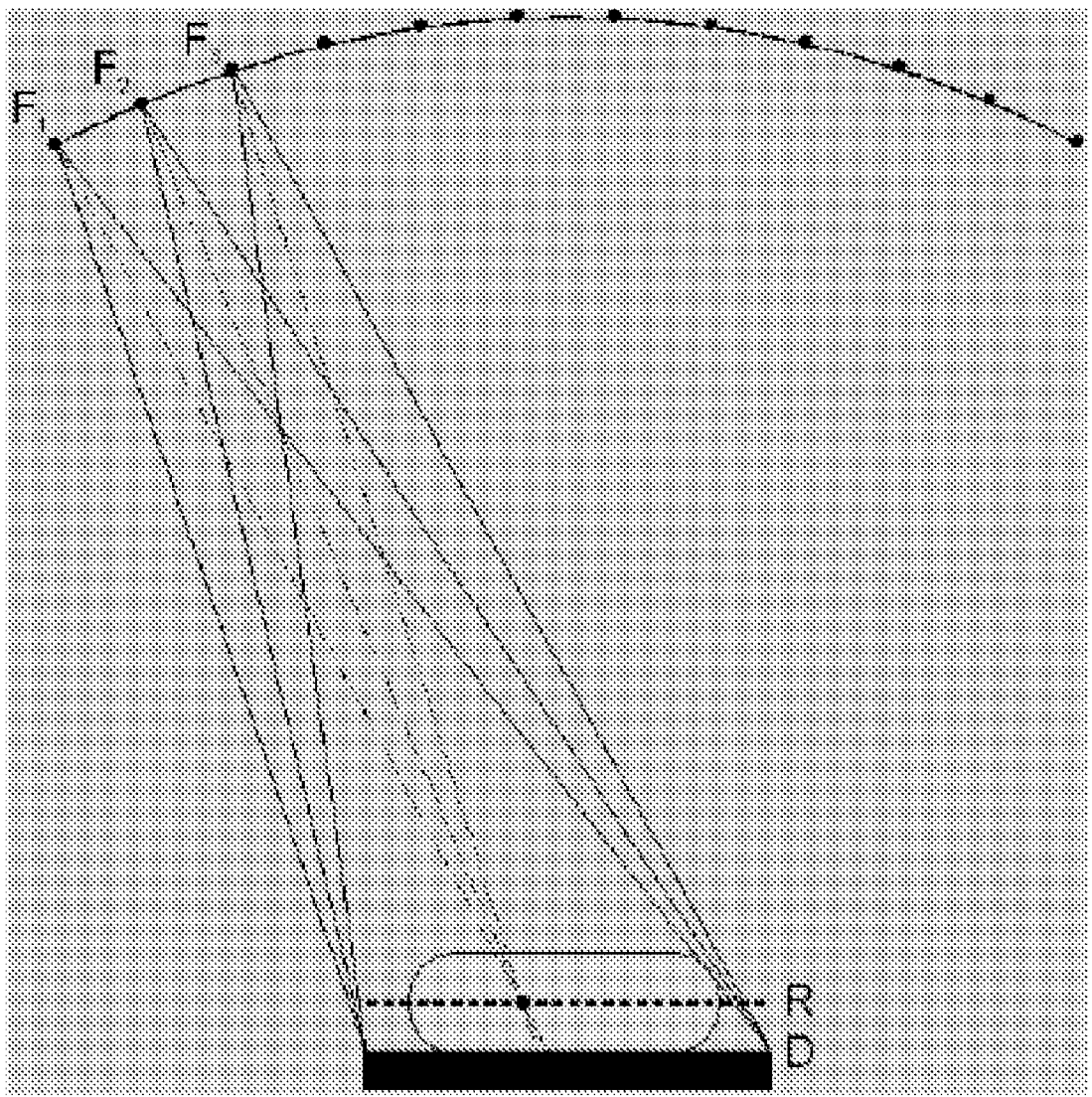
FIGS. 1A-1D illustrate examples of acquisition geometries for limited angle computed tomography or tomosynthesis.

Referring to the acquisition geometry illustrated in FIG. 1A, for a given spatial coordinate (x, y, z) in the anatomy (in this case, a compressed breast) at a plane R, one sets t=1, and applies the formula to calculate (u, v, s) in the image $D_i$. The physical location in the projection image plane, $D_i$, is (u/s, v/s). In this way, one may create a backprojected image $R_i$ from the projection image $D_i$ pixel-by-pixel.

The backprojection step 506 is repeated for each of the N images, and the process proceeds to step 508 where each of the backprojected images are combined. For the simple backprojector, the final reconstruction for plane R is given by the sum of the individual backprojections. One embodiment may be expressed as a weighted sum of the projections, such that:

$$R = \frac{\sum R_t}{\sum w_t} = \frac{\sum (I_t * w_t)}{\sum w_t}$$

Note that A is not necessarily constant across the anatomy; $a_{ij}$ may differ in value for different areas of the image depending on the acquisition geometry. Also note that an equivalent method is to calculate the image data coordinates (u, v) directly from the spatial coordinates (x, y, z).

Similarly, although the reconstructed image, R, is described as a plane, it is relevant to note that the surface of reconstruction does not need to be a plane. The proposed reconstruction method may allow the user to reconstruct images on arbitrary surfaces that are smooth and continuous. For example, it may be possible to define a surface that follows the path of a blood vessel and reconstruct the backprojected image on that surface. In that way, the blood vessel may be in focus along its entire length. In this instance, the geometry of the surface may be more fully specified by dividing the surface into a plurality of small regions (e.g., small triangles or linear strips). It is important to note, however, that the range of angles for which tomosynthesis provides mathematically consistent reconstructions may be limited to the range of angles acquired. Thus, care may be taken in determining what reconstructions will be presented.

During backprojection, the projection images are spatially translated in accordance with the geometry of the acquisition system and the image plane. The projected images are interpolated and summed, taking into account the weightings of each pixel.

To illustrate backprojection, an exemplary acquisition geometry used in tomosynthesis is provided in previously discussed FIG. 1A. In this acquisition system, the x-ray focus may be sequentially positioned at multiple locations ($F_1$, $F_2$, $F_3$, . . . ). At each location ($F_i$), a projection image of the anatomy may be made onto the detector to produce an image ($D_i$). For illustration, the foci are shown in an arc with equal spacing; in fact, the location of the foci may be arbitrary. Similarly, the detector is shown to be held rigidly; again, this is only for the purposes of illustration; the detector may also be oriented in an arbitrary manner.

Figure 1B:
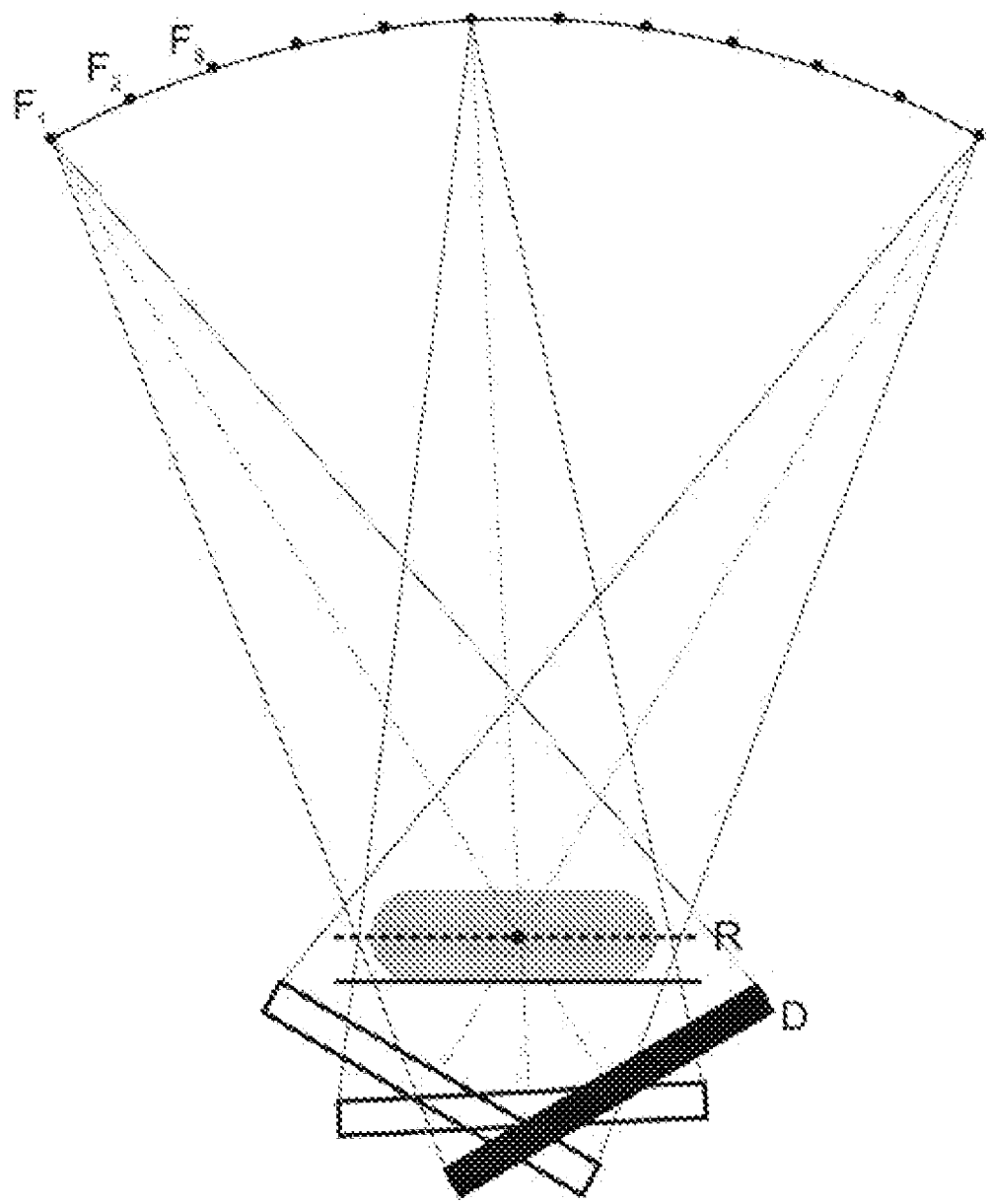
Figure 1C:
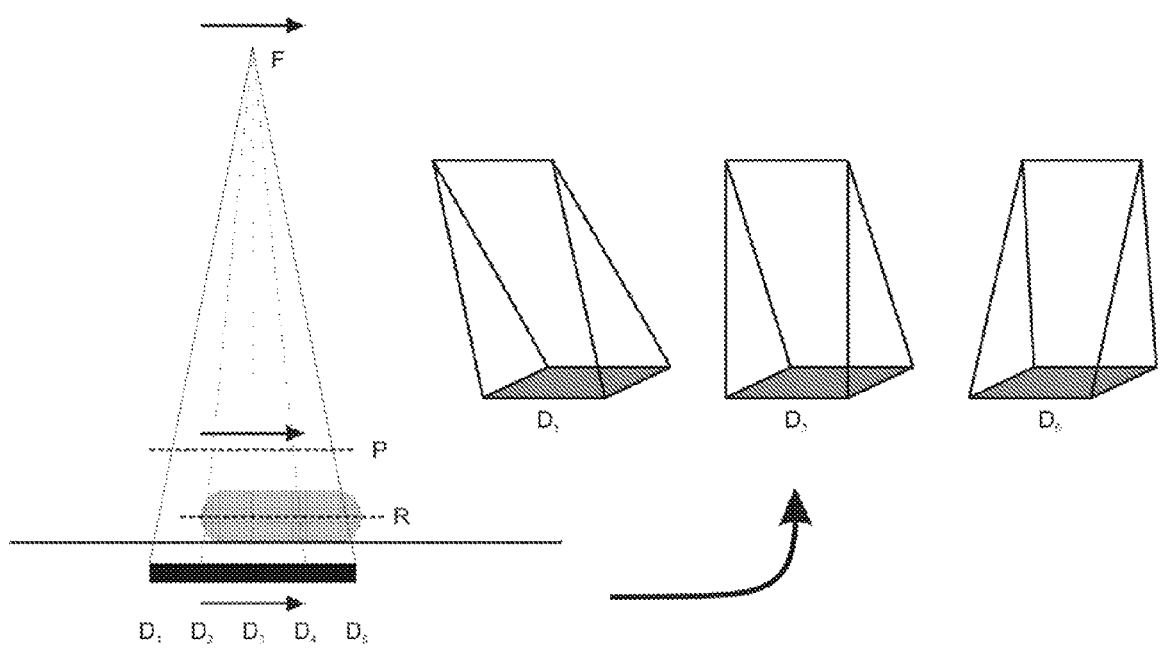
Figure 1D:
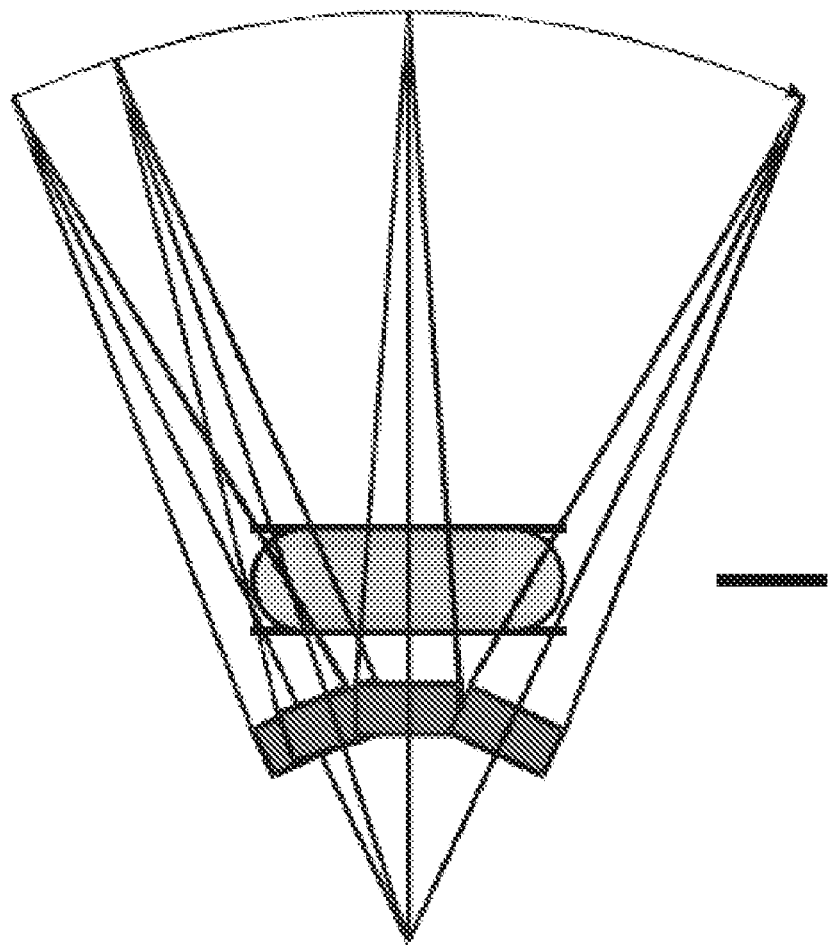

For some acquisition geometries, the data acquired during tomographic and tomosynthesis imaging are 2D projections that are continuous in a plane, such as those illustrated in FIGS. 1A and 1B. The native formats of these projection data are well-suited to BPF. For geometries such as those illustrated in FIGS. 1C and 1D, the x-ray focus is moved continuously as a set of discrete detectors sequentially record projection data. The image data acquired by a single detector ($d_i$) is sorted over the multitude of source x-ray positions, so as to produce an image ($D_i$) which corresponds to a single projection of the anatomy. Although this is called a projection, it does not need to be truly projective in the mathematical sense provided the resultant backprojected image is continuous after all projections are processed.

Figure 6:
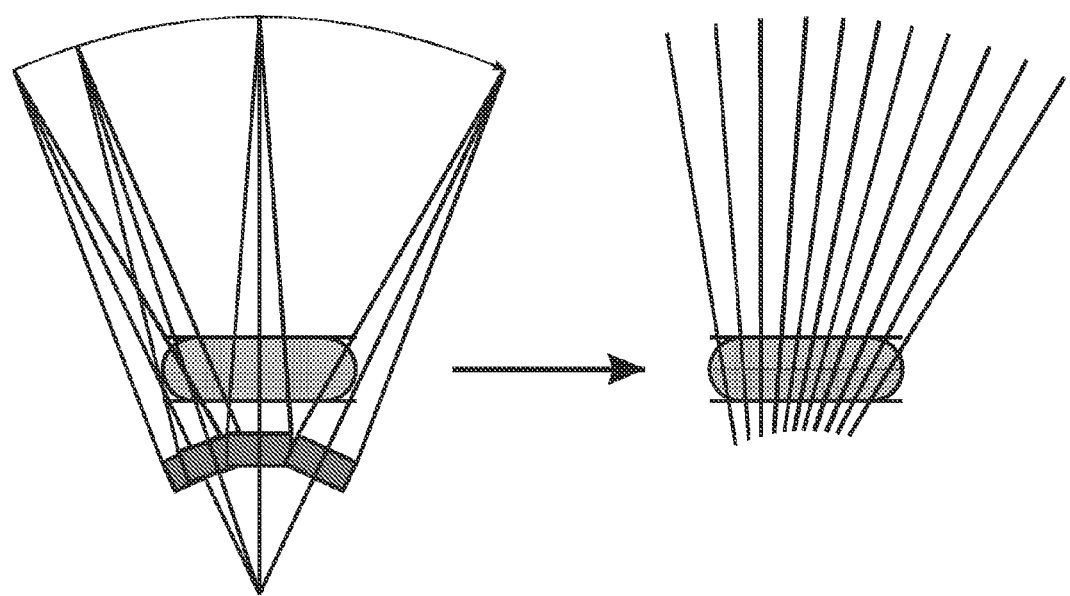
FIG. 6 illustrates an exemplary image acquisition geometry and reconstruction technique according to one embodiment of the present invention.

FIG. 6 is an exemplary image acquisition geometry and reconstruction technique according to one embodiment of the present invention. On the left, the x-ray focus is moved continuously while a small number of discrete linear detectors produce a sequential set of linear images of an anatomy, similar to the discussion of FIG. 1D above. On the right side of FIG. 6, the images are sorted and projected. By performing this sorting and projection step for each detector, a tomosynthesis image at any point in the anatomy may be created.

Figure 7:
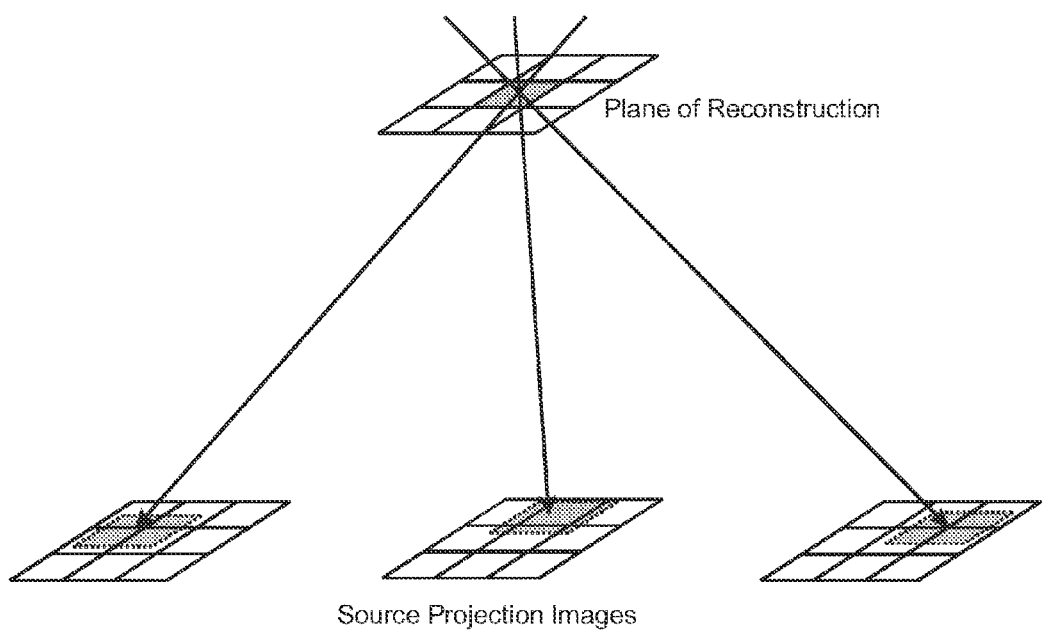
FIG. 7 illustrates an exemplary schematic of a pixel reconstruction during backprojection according to an embodiment of the present invention.

FIG. 7 illustrates an example of a reconstruction method in which a pixel in the plane of reconstruction (equal in size and location to a single pixel on the screen of the computer display) is backprojected to different locations in the various source projection images based upon varying field of view settings by a user. The backprojected data must be sampled and/or interpolated to be rendered in the plane of reconstruction in multiple locations based upon any pan or zoom transformation information. It should be noted that additional methods of sampling may be used, and the method shown in FIG. 7 is merely presented as an example.

Figure 8:
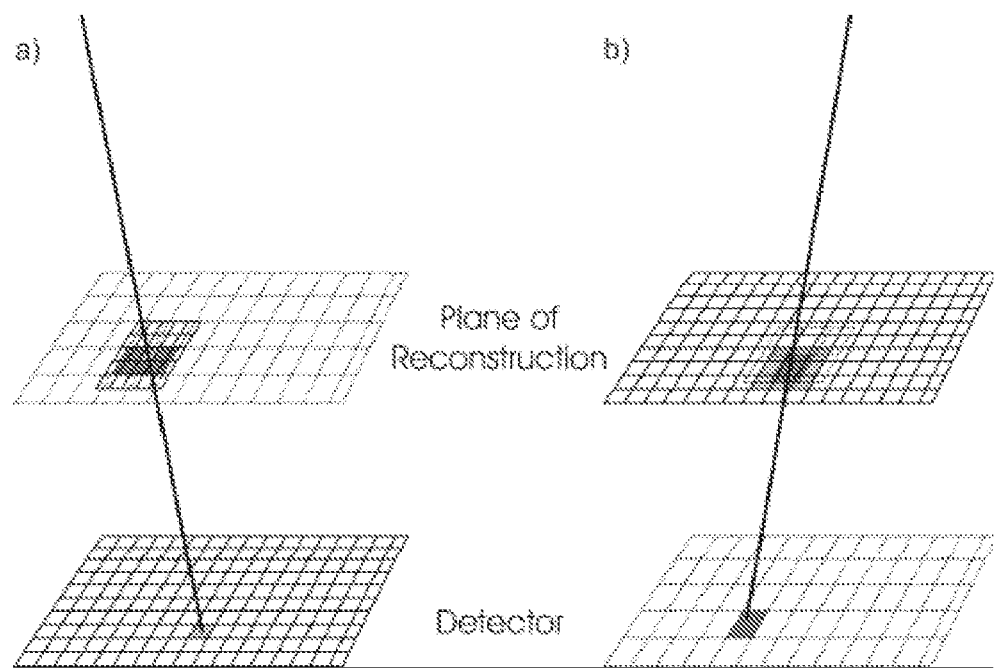
FIG. 8 illustrates an exemplary schematic of pixel interpolation during backprojection according to an embodiment of the present invention.

When the image is interpolated, image quality is preferably preserved. The interpolation algorithm must be designed to handle the two situations shown in FIG. 8. In FIG. 8, the left image illustrates the magnification in the rendered plane (the upper plane of pixels) is such that many detector pixels project onto the same pixel in the reconstructed plane. The interpolation algorithm may include a weighted sum of these rays, so that any x-ray quantum noise in the reconstructed image is kept small. At the same time, the interpolation algorithm must also handle the situation where the magnification of the rendered plane is such that one detector pixel projects to many pixels in the reconstructed plane (right image of FIG. 8). Failure to do so may result in some pixels having no texture mapped to them; in that instance, "holes" would appear in the reconstruction, resulting in a lower image quality. The interpolation algorithm consists of any of those known to one skilled in the art, such as pixel replication, bilinear interpolation, bi-cubic interpolation, etc.

A second sample backprojector is an "ordered-subset backprojector". The ordered-subset backprojector builds upon the simple backprojector in which one or more contributions are eliminated from the reconstruction. One example of an ordered-subset backprojector finds the minimum value R* and eliminates its contribution from the reconstruction. One result of this algorithm is to reduce artifacts from attenuating objects, such as large calcifications and surgical clips that are located out of plane. Other statistical tests could be used, including absolute elimination, elimination if less than the mean, or elimination if it exceeds a multiple of the standard deviation at a given pixel location. In addition, other statistical values such as the mode or median may be used. One embodiment may be expressed by the following formula:

$$R = \frac{\sum R_t}{\sum w_t} - \frac{R^*}{w^*}$$

A third sample backprojector is a "convex-hull backprojector". In the convex-hull backprojector, the projection images are compared against a threshold to segment the region of the interest from the background. The logical AND of the N thresholded projections of the anatomy determines the convex hull. Thus, the logic operations to determine the convex-hull are given by the following sample pseudo code:

```
If R_i = AIR then
    R = AIR;
Else
    R = f(R_t);
```

The calculation of the convex-hull enables a post-processing technique of inverting the image pixel intensity (i.e. white pixels become black and vice versa). Inverting image intensity is a common imaging feature used by a radiologist when reading diagnostic images. This may be done by inverting the gray-level scale in the image. The background (or area outside of the object) is typically not inverted as a white background tends to blind the radiologist. By checking if the weightings indicate whether a given pixel is outside the object (i.e. air) and, if so, the pixel intensity is not inverted and the background may be constantly set to black.

In DBT, the calculation of the convex-hull may result in the segmentation of the breast from the background (an attenuation path solely through air) which has the effect of eliminating artifacts that encircle the breast in the reconstruction. By segmenting the breast from the background, the background may be set to black regardless of the polarity of the grayscale used for the breast; that is, the background would remain black when the grayscale in the breast is inverted. This is a beneficial feature for displaying breast images, as many radiologists believe that calcifications are easier to see if rendered black on white (as opposed to the standard white on black). Again, this demonstrates the advantage of backprojecting the image data before filtering, as this significantly simplifies the reconstruction method.

The above backprojectors may be used separately or combined. Note that although the preferred formulaic embodiments are described for each backprojector, other formulaic embodiments that achieve the same effect are possible.

Referring again to FIG. 5, once combined in a single 3D tomographic image, the algorithm proceeds to step 510. Here, the image is filtered. Images produced by back-projection without filtering appear blurred. As a result filtering is applied to images in all backprojection schemes. Backprojection before filtering offers advantages in terms of reduced complexity and greater flexibility. A number of filters may be applied to the reconstructed images, including convolution, unsharp masking and fast Fourier transforms. As with other aspects of DRR, preference is given to fast, high quality filter algorithms.

After filtering is applied to the images, the algorithm proceeds to step 512 where additional post-processing may be applied. As mentioned in the description of the DRR algorithm, these post-processing steps may include pixel inversion, flipping, rotation, and additional statistical conditioning, such as de-noising. Following post-processing, the result is a 3D tomographic image such as image 520.

Though both the FBP and BPF algorithms above have been described generically, both algorithms may be equally implemented on a GPU with the methods discussed above. However, BPF is computationally expedient for DRR whereas FBP will delay the first reconstruction and result in longer delays when the filters are changed.

The reconstruction of 3D tomographic images from its source projection images is a computationally intensive process due to the amount and complexity of the data. For practical use in a medical clinic, manufacturers of CT systems have relied on the use of customized hardware, such as ASICs and FPGAs, for image reconstruction at speeds that support the clinical workflow. However, these hardware solutions are extremely expensive and highly customized which makes them inflexible for modification and generalization.

In DBT, a 3D tomographic image of the breast is reconstructed from a set of 2D projection images taken over a limited range of angles. Current tomosynthesis reconstruction methods vary from 5 to 30 minutes to reconstruct one 3D image dataset per breast. For DBT to be clinically viable, a rapid reconstruction time is necessary to address the need for high-throughput.

Figure 9:
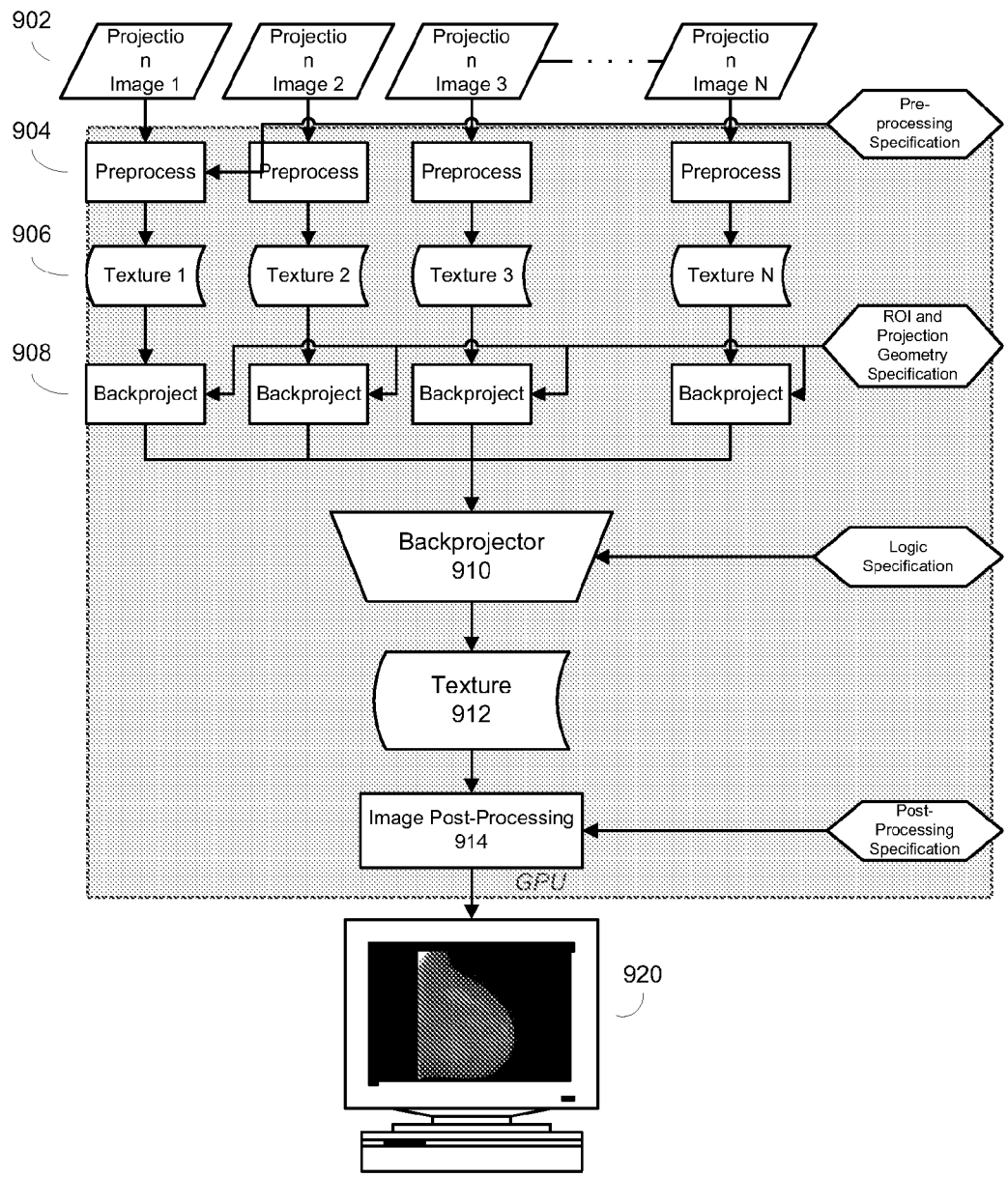
FIG. 9 illustrates an exemplary flow diagram of one dynamic reconstruction method on a graphics processor unit.

FIG. 9 illustrates a GPU-based image reconstruction process that provides both real-time and on-demand image processing. The process begins at step 902 where the individual source projection images are loaded into memory. After each projection image is in memory, the image data may be preprocessed at step 904. In general, preprocessing only needs to be performed once after the image data is loaded and may be performed on the CPU or the GPU. The type of preprocessing depends on the reconstruction method being implemented. In FBP, the projection images may be pre-filtered to enhance specific structures in the projection images and to reduce the blurring after backprojection. In BPF, the source image data may be preprocessed to optimize the reconstruction time by rejecting data that is invalid by the assignment of weightings and processing only data that will contribute to the reconstructed image, as discussed in the section describing the Backprojection Filtering algorithm.

After preprocessing, the process proceeds to step 906. Each source projection image may be loaded into GPU memory where these data may be stored as texture objects.

The process then proceeds to step 908 where backprojection of the images may be performed using a projective transform as described in the BPF algorithm description. The projection image may be mapped to the reconstructed plane in the fragment processor(s). The interpolated coordinate is projected to the real 2D texture coordinate, (u/s, v/s), to index into the texture image.

The interpolation of the textures is performed in the fragment processors. The fragment shading program code must be carefully implemented to preserve image quality. The interpolation scheme is be repeated for each focus location; in each instance after the first focus location, the projected texture images may be summed.

Certain other embodiments include fast interpolation methods that more coarsely sample the image data. One possible implementation is to set certain ray weightings to zero. For weightings of zero, the contribution of that pixel data may be ignored when combining the projection images.

For embodiments that support DRR, the reconstruction of the image may be pixel-driven, meaning only those pixels as defined by a scaled ROI are reconstructed. This ROI is typically defined as a plane segment in 3D, thus both the position of the plane and the field-of-view (pan and zoom) of the display region need to be specified. The screen image is clipped to this ROI; no calculations are performed outside the ROI to avoid unnecessary computation. The level of detail in the image is determined by the size of the screen (in pixels), and the size of the ROI (as measured physically in the object in units of length). This is compared to prior art that is non-DRR in which tomographic images are reconstructed with fixed image size and resolution.

For the DRR approach then the texture coordinate (u, v, s) corresponding to an image may be calculated for a spatial coordinate in the ROI (x, y, z) using the following equation.

$$\begin{bmatrix} u \\ v \\ s \end{bmatrix} = P \cdot \begin{bmatrix} x \\ y \\ z \\ t \end{bmatrix},$$

where P is a parameterized transform that maps the spatial coordinate (x, y, z) in the ROI to the reconstructed plane in the object coordinates to the detector plane. For the BPF algorithm, the transform P contains the projective geometry matrix A described in the BPF algorithm. This is key to DRR on a GPU.

Figure 10:
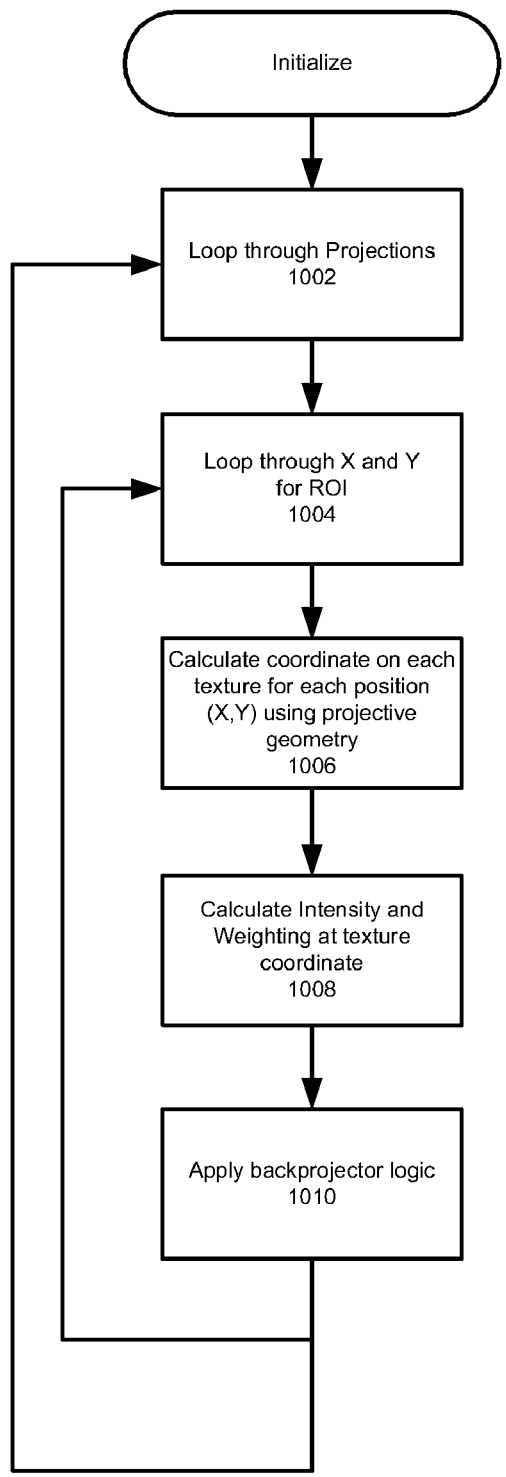
FIG. 10 illustrates an exemplary algorithm for calculating pixel intensity.

After backprojection at step 908, the process proceeds to step 910 where the tomographic image is reconstructed. FIG. 10 illustrates the algorithm for calculating the intensity for each pixel in the reconstructed image. The algorithm begins when the first projection image is selected from the set of projection images at step 1002. The algorithm is then looped through the X and Y coordinates of the specified ROI within the image in step 1004. Each pixel in the ROI is backprojected and interpolated using the transform, P (discussed above), to determine the corresponding coordinate in each projective texture in step 1006. For each texture coordinate, the corresponding pixel intensity and weighting are calculated in step 1008. Additional backprojector logic is then applied to determine the final pixel output in step 1010 and the process returns to steps 1002 and 1004.

An example of general pseudo code for the backprojection combination may be as follows:

```
Loop i for Number_of_Projections
    Loop (x,y) for region of interest
        Intensity += Sampler(i, u, v) * weight(i, P(x), P(y));
        Weight += weight(I, P(x), P(y));
    end loop
end loop
Reconstructed_Pixel_output = f(Intensity(;),Weight(;));
```

It should be noted the intensity of a pixel on the reconstructed plane, R, is calculated in the final step of the pseudo code (i.e. $R=f(R_i)=f(I_i,w_i)$ where I and w are the intensity and weighting of the pixel, respectively). The function f (or backprojector) calculates the pixel output using the pixel data and weightings from each source projection after backprojection and interpolation.

In the BPF algorithm, three sample backprojectors were defined (i.e., Simple Backprojector, Ordered Subset Backprojector and Convex-Hull Backprojector). All three backprojectors may be implemented on the GPU separately or combined.

Referring again to FIG. 9, after the image is reconstructed at step 910, it is stored in a temporary texture at step 912. After storage, the process proceeds to step 914 where any post-processing may be performed.

A number of post-processing steps 914 may be applied to the reconstructed image to improve image quality. These post-processing steps may include filtering, pixel inversion, flipping, rotation, and statistical conditioning. In embodiments that support DRR where the image is immediately displayed, the window and level may be applied at this point.

A number of GPU manufacturers have implemented filtering functions within the graphics hardware. These include convolution, unsharp masking and fast Fourier filtering. Alternatively, customized filters may be implemented as shader programs and applied to the image as it passes through the GPU pipeline. This may be done by rendering the image to a temporary texture pixel for pixel using an orthographic projection geometry.

Another example of post-processing is flipping the reconstructed image about the vertical and horizontal axes. This may be done by including a transform to the projective geometry during the backprojection that flips the image. Alternatively, the image texture may be transposed as it is rendered to the frame buffer.

After the post-processing step 914, the reconstructed and post-processed image is rendered to the frame buffer and then displayed to the screen in step 920. The image is rendered to the computer monitor pixel for pixel using an orthographic projection geometry.

As discussed herein, the present invention is implemented on a computer with a suitable computing environment. A computer includes one or more processor units (for example, Intel, AMD or Motorola), random-access memory, read-only memory, one or more GPUs, one or more mass storage devices, one or more graphic displays and a system bus that connects the processor unit to the various system components.

Embodiments are described in terms of a computer executing computer-executable instructions. However, some embodiments can be implemented entirely in computer hardware in which computer-executable instructions are implemented in ROM only. Some embodiments can also be implemented in client/server computing environments where remote devices that perform tasks are served through a computer communications network. Program modules can be located in both local and remove memory storage devices in a distributed computing environment.

Additional embodiments may include implementing the BPF reconstruction algorithm on a GPU on a server without a display in a conventional mode whereby reconstructions are performed by a separate computing device.

While several embodiments of the invention have been described herein by way of example those skilled in the art will appreciate that various modifications, alterations, and adaptations to the described embodiments may be realized without departing from the spirit and scope of the invention defined by the appended claims.

We claim:

1. A method of dynamically reconstructing three dimensional (3D) tomographic images from a set of projection images, the method comprising:
    loading a set of projection images into a memory device;
    determining a reconstruction method for the set of projection images;
    reconstructing a three dimensional 3D tomographic image from the set of projection images to be displayed to a user;
    performing any post reconstruction processing on the reconstructed 3D tomographic image; and
    rendering and displaying the reconstructed 3D tomographic image.

2. The method of claim 1, wherein said set of projection images are acquired by standard tomographic or tomosynthesis image acquisition techniques.

3. The method of claim 1, wherein a plane of reconstruction is arbitrarily chosen by the user.

4. The method of claim 3, wherein the plane of reconstruction is based upon a region of interest (ROI) selected by the user, wherein the ROI is incorporated into image reconstruction to eliminate unnecessary computation during reconstruction.

5. The method of claim 4, wherein changes to the ROI results in a reconstruction of the 3D tomographic image, providing a high-quality magnification of the 3D tomographic image.

6. The method of claim 4, wherein selecting the ROI allows the 3D tomographic image to be reconstructed on an arbitrary surface.

7. The method of claim 1, further comprising preprocessing each image in said set of projection images prior to said reconstructing the 3D tomographic image.

8. The method of claim 7, wherein said preprocessing includes performing at least one of the following steps: rescaling each of the set of projection images to be proportional to a logarithm of any x-fluence; equalizing x-ray intensity in each of the set of projection images to account for an increased attenuate of an object at oblique angles; masking defects in each of the set of projection images; apodizing each image in the set of projection images; segmenting a desired object in each of the set of projection images from a non-desired object in each of the set of projection images; and performing a thickness equalization method in each of the set of projection images.

9. The method of claim 8, wherein masking defects in each of the set of projection images, apodizing each image in the set of projection images and segmenting a desired object in each of the set of projection images are performed by weighting each pixel in a source projection image and adjusting the 3D tomographic image based upon these weightings.

10. The method of claim 1, further comprising saving the 3D tomographic image in the memory such that a user may access and view the 3D tomographic image.

11. The method of claim 10, wherein the set of projection images are saved in the memory along with the 3D tomographic image such that a new 3D tomographic image can be constructed from the saved set of projection images.

12. The method of claim 11, wherein the saved 3D tomographic image is forwarded to another system for viewing.

13. The method of claim 1, wherein the post-processing includes performing one or more of following: filtering, flipping, rotating, inverting the pixel intensity, and statistical conditioning of the 3D tomographic image.

14. The method of claim 13, wherein filtering further comprises dynamically applying a filter to the 3D tomographic image while the 3D tomographic image is being viewed by the user.

15. The method of claim 1, further comprising alternatively projecting the 3D tomographic image and the set of projection images, wherein any switching between the 3D tomographic image and the set of projection images is performed in response to a user selection.

16. The method of claim 15, wherein the set of projection images are backprojected by at least one of the following: a simple backprojector, an ordered subset backprojector, and a convex-hull backprojector.

17. The method of claim 16, wherein the simple backprojector is configured to sum each backprojection of the set of projection images, thereby resulting in a 3D tomographic image.

18. The method of claim 16, wherein the ordered subset backprojector is configured to eliminate one or more contributions from a 3D tomographic image, thereby eliminating any unwanted artifacts in the 3D tomographic image.

19. The method of claim 16, wherein the convex-hull backprojector is configured to segment an object in the 3D tomographic image from any background of the 3D tomographic image, thereby eliminating any unwanted artifacts in the 3D tomographic image.

20. The method of claim 16, wherein the simple backprojector, the ordered subset backprojector and the convex-hull backprojector may be used individually or in combination.

21. The method of claim 1, wherein loading a set of projection images into a memory device further comprises loading each of the set of projection images into a graphic processing unit memory, wherein each of the set of projection images is stored as a texture object.

22. The method of claim 1, wherein a single image of the set of projection images is acquired by a single detector over a multitude of x-ray positions.

23. The method of claim 1, wherein at least one combination of reconstruction parameters and filters are defined.

24. The method of claim 23, wherein a new 3D tomographic image is reconstructed in response to a user selection of a reconstruction parameter or filter.

25. A method of dynamically reconstructing 3D tomographic images from a set of projection images, the method comprising:
    loading a set of projection images into a memory device;
    determining a reconstruction method for the set of projection images;
    determining a region of interest in the set of projection images;

reconstructing a three dimensional image from the set of projection images focusing on the determined region of interest to be displayed to a user;

performing any post reconstruction processing on the reconstructed 3D tomographic image; and rendering and displaying the reconstructed 3D tomographic image.

26. The method of claim 25, wherein said set of projection images are acquired by standard tomographic or tomosynthesis image acquisition techniques.

27. The method of claim 25, further comprising preprocessing each image in said set of projection images prior to said reconstructing the 3D tomographic image.

28. The method of claim 25, further comprising saving the 3D tomographic image on the memory such that a user may access and view the 3D tomographic image.

29. A method of dynamically reconstructing and rendering a 3D tomographic image on demand from a set of projection images, the method comprising the steps of:

loading said set of projection images into memory;

selecting a region of interest;

selecting a reconstruction method;

reconstructing an image according to said reconstruction method to produce a 3D tomographic image focusing on said region of interest;

performing any post reconstruction processing on the 3D tomographic image; and rendering said 3D tomographic image on a display.

30. The method of claim 29, wherein said region of interest is selected based upon a set of user inputted plane of reconstruction and field of view parameters.

31. The method of claim 29, wherein said reconstruction is performed by a graphics processing unit.

32. The method of claim 29, wherein said reconstruction is at least one of a single pass reconstruction algorithm, a multi-pass iterative reconstruction algorithm, and a Fourier reconstruction algorithm.

33. A method of dynamically reconstructing three dimensional (3D) tomographic images from a set of projection images, the method comprising:

loading a set of projection images into a memory device;

preprocessing each image in said set of projection images, wherein preprocessing includes performing at least one of the following:

rescaling each of the set of projection images to be proportional to a logarithm of any x-fluence, equalizing x-ray intensity in each of the set of projection images to account for an increased attenuate of an object at oblique angles, masking defects in each of the set of projection images, apodizing each image in the set of projection images, segmenting a desired object in each of the set of projection images from a non-desired object in each of the set of projection images, and performing a thickness equalization method in each of the set of projection images;

determining a reconstruction method for the set of projection images;

reconstructing a three dimensional 3D tomographic image from the set of projection images to be displayed to a user; and performing any post reconstruction processing on the 3D tomographic image.

* * * * *